(12) United States Patent
Kontschieder et al.

(10) Patent No.: US 7,297,241 B2
(45) Date of Patent: Nov. 20, 2007

(54) METHOD AND A DEVICE FOR MONITORING A MEDICAL MICROSAMPLE IN THE FLOW MEASURING CELL OF AN ANALYZER

(75) Inventors: Heinz Kontschieder, Graz (AT); Herfried Huemer, Feldbach (AT); Martin Hajnsek, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 688 days.

(21) Appl. No.: 10/646,109

(22) Filed: Aug. 22, 2003

(65) Prior Publication Data

US 2006/0011493 A1    Jan. 19, 2006

(30) Foreign Application Priority Data

Aug. 23, 2002    (AT) .............................. A 1267/2002

(51) Int. Cl.
*G01N 27/327*    (2006.01)
(52) U.S. Cl. ................. 204/403.01; 204/406; 204/409; 205/792
(58) Field of Classification Search ........ 204/409–412, 204/401, 403.1; 205/775, 792
See application file for complete search history.

(56) References Cited

U.S. PATENT DOCUMENTS

| | | | |
|---|---|---|---|
| 3,676,321 A | | 7/1972 | Cummings et al. |
| 3,811,841 A | * | 5/1974 | Kassel .......................... 422/82 |
| 4,511,659 A | * | 4/1985 | Matson ..................... 205/780.5 |
| 4,919,770 A | | 4/1990 | Preidel et al. |
| 4,929,426 A | * | 5/1990 | Bodai et al. ................... 422/63 |
| 5,097,834 A | | 3/1992 | Skrabal ....................... 128/632 |
| 5,130,009 A | * | 7/1992 | Marsoner et al. ...... 204/403.11 |
| 5,284,568 A | * | 2/1994 | Pace et al. .............. 204/403.03 |
| 5,438,271 A | | 8/1995 | White et al. |
| 5,763,795 A | * | 6/1998 | Tanaka et al. ............ 73/863.73 |
| 6,447,657 B1 | * | 9/2002 | Bhullar et al. ......... 204/403.01 |
| 6,544,393 B1 | * | 4/2003 | Kunnecke .................... 204/409 |
| 6,645,368 B1 | * | 11/2003 | Beaty et al. ................. 205/792 |
| 6,723,216 B2 | * | 4/2004 | Taagaard et al. ............ 204/401 |
| 6,872,299 B2 | * | 3/2005 | Kermani et al. ......... 205/777.5 |
| 7,022,218 B2 | * | 4/2006 | Taniike et al. ........... 205/777.5 |

FOREIGN PATENT DOCUMENTS

EP    1 312 919 A2    5/2003

(Continued)

*Primary Examiner*—Nam Nguyen
*Assistant Examiner*—Surekha Vathyam

(57) ABSTRACT

The invention relates to a method and device for the monitoring of a medical microsample in the flow measuring cell of an analyzer with regard to position and absence of bubbles by means of an alternating voltage applied to the measuring cell, the measuring cell being provided with a multitude of electrode systems placed one behind the other, each system comprising a number of single electrodes for measuring a substance contained in the microsample by means of a measurement voltage which essentially is a DC voltage. To monitor the exact position of the microsample and/or to detect air bubbles in the area of each electrode system, the alternating voltage and the measurement voltage are simultaneously and directly applied to the single electrodes of the corresponding electrode system, and the measured AC component respectively the measured impedance gives a measure for the position of the microsample and the absence of bubbles.

11 Claims, 3 Drawing Sheets

FOREIGN PATENT DOCUMENTS

| | | |
|---|---|---|
| JP | 59-125052 | 7/1984 |
| JP | 59125052 | 7/1984 |
| JP | 2-179456 | 7/1990 |
| JP | 02-030763 | 8/1990 |
| JP | 03-223665 | 10/1991 |
| JP | 04-125459 | 4/1992 |
| JP | 10-253610 | 9/1998 |
| JP | 2001-141694 | 5/2001 |
| JP | 2001-174430 | 6/2001 |
| WO | WO 99/32881 | 7/1999 |

* cited by examiner

METHOD AND A DEVICE FOR MONITORING A MEDICAL MICROSAMPLE IN THE FLOW MEASURING CELL OF AN ANALYZER

FIELD OF THE INVENTION

The present invention relates to monitoring systems and methods thereof, and in particular to a device and method for monitoring a medical microsample in the flow measuring cell of an analyzer.

BACKGROUND OF THE INVENTION

In measuring medical samples a fundamental distinction is made between one-way sensors and flow measuring cells. In the case of a one-way sensor the sample is introduced into the sensor and brought into contact with measuring electrodes. The basic requirement for an accurate and error-free measurement is a suitable positioning of the sample in the measuring cell. It is a known procedure to check the positioning via special measuring contacts, to which an AC voltage is applied, such that an impedance measurement will produce a signal which provides information regarding the position of the sample. Due to the distance between the electrodes for the measurement proper and the electrodes for position-checking, errors in the measurement result may occur.

From WO 99/32881 a one-way measuring cell is known which avoids the above disadvantage by applying an alternating voltage to the measuring electrodes themselves. It is possible in this way to check the exact positioning of the sample as a first step and then to proceed to the measurement itself or to reject the sample if the positioning is found to be at fault. Furthermore, flow cells with a multitude of electrode systems are unknown, which are suitable for a series of measurements or for continuous measurement and which determine the concentration of diverse analytes in a sample. Conditions in flow cells of this sort differ fundamentally from those in one-way cells. It is for instance not sufficient in this type of flow cells to check the positioning of the sample prior to measuring, as it will of course change during the measurement process. A further problem occurs if electrochemical reactions due to the measurement voltage cause bubble formation at an electrode, which is undesirable and may result in measurement errors.

SUMMARY OF THE INVENTION

It is against the above background that the present invention provides certain unobvious advantages and advancements over the prior art. In particular, the inventors have recognized a need to improve methods and/or devices for monitoring the positioning and the absence of bubbles in a medical microsample in the flow cell of an analyzer in such a way, that reliable measurement results may be obtained in flow cells with a multitude of electrode systems and that a simple design is guaranteed.

This object is achieved by the various embodiments of the present invention by providing that both the alternating voltage and the measurement voltage are simultaneously and directly applied to the single electrodes of the respective electrode system and by using the measured AC component or the measured impedance as a measure for the position of the microsample and the absence of bubbles. According to an embodiment of the present invention, the alternating voltage—for example, for measuring impedance or conductance—is coupled in via two single electrodes of the electrode system that are already used for measuring a substance contained in the sample.

Although the present invention is not limited to specific advantages or functionality, the following is noted:

The measuring cell need not be provided with additional electrodes for applying the alternating voltage, i.e., for impedance measurement.

Impedance measurement may directly be used to detect undesirable air bubbles in the area of the respective electrode system. The presence of bubbles is indicated by a change in impedance or conductance.

Air bubbles are detected in places where their presence would negatively influence the measurement result (for instance, adhering to an electrode or counter-electrode), but are ignored in places where they do not influence the measurement result (i.e., at the walls of the measuring cell).

The quality of the wetting of single electrodes of the electrode system may be assessed (for instance, when measuring glucose or lactate).

Impedance measurement may also be used to determine the exact positioning of the microsample in the area of each single electrode in sample channels with a multitude of electrode systems, thus permitting the sample volume to be kept small. According to the invention the microsample in this case is moved along in the flow cell until a predetermined impedance or conductance value is obtained, which indicates that the microsample is exactly positioned in the area of the relevant electrode system.

Measurement of the impedance or conductance may take place simultaneously with the measurement of the substance in the microsample.

Simultaneous measurement offers the advantage that a change in the sample taking place during analyte measurement (e.g., gas formation at the working electrode, change in pH value, etc.) may be monitored via the simultaneous conductance measurement at the exact point in time of the analyte measurement.

In accordance with the various embodiments of the present invention, repetitive measurements of microsamples with short cycle times may be carried out with high precision and reliability. The occurrence of gas bubbles can be recognized immediately during the measurement process and may thus be taken into account. A further advantage in comparison to measurement with one-way sensors lies in the fact that in serial measurements the time-consuming and awkward replacement of the sensors, which often entails a time-intensive calibration of the sensor, is avoided.

In accordance with the various embodiments of the present invention, the possibility to determine the position of the sample during measurement permits a substantial reduction in sample volume as compared with state-of-the-art methods; an advantage which becomes increasingly important as the number of analytes to be measured increases.

In accordance with one embodiment of the present invention, a device for monitoring a medical microsample in a flow measuring cell of an analyzer is provided comprising at least one electrode system comprising at least two single electrodes positioned within the flow measuring cell, and a circuit for producing the voltages to be applied to the single electrodes. The electrode system is configured for measurement of at least one substance contained in the microsample by application of a measurement voltage which is essentially a DC voltage, and detection of absence of bubbles and/or positioning of the microsample by application of an alternating voltage to the flow measuring cell. Both the alternating voltage and the measurement voltage are simultaneously and directly applied to the single electrodes of the respective electrode system, and the measured AC component or the measured impedance provides a measure for the position of the microsample and the absence of bubbles. The circuit has a summation point at which the alternating voltage for the purpose of monitoring the medical microsample with regard to position and absence of bubbles is superposed on the DC voltage serving as measurement voltage.

In accordance with another embodiment of the present invention, a method for monitoring a medical microsample in a flow measuring cell of an analyzer is provided comprising providing an analyzer including a flow measuring cell and a device comprising at least one electrode system, each system comprising at least two single electrodes; introducing a microsample into the flow measuring cell, the microsample passing the electrode system; measuring at least one substance contained in the microsample by applying a measurement voltage to the flow measuring cell, which measurement voltage is essentially a DC voltage; and detecting the absence of bubbles and/or position of the microsample in an area of the at least one electrode system by applying an alternating voltage to the flow measuring cell simultaneous with the measurement voltage via two single electrodes of the at least one electrode system, and detecting the AC component or impedance measured.

The device according to an embodiment of the present invention is suitable for electrode systems comprising one working electrode and one reference electrode (pseudo-reference electrode), where both electrodes serve as electrical contacts for the impedance measurement between working electrode and reference electrode, as well as for three-electrode systems comprising a working electrode, a counter-electrode and a reference electrode, where the working electrode and the counter-electrode serve as electrical contacts for the measurement of the impedance between working electrode and counter-electrode.

For the detection of air bubbles, in accordance with an embodiment of the present invention, a counter-electrode can be placed both in front of and behind the working electrode in the direction of flow of the micro-sample, the two counter-electrodes being electrically short-circuited.

Another advantageous variant or embodiment of the present invention provides that the counter-electrode and the working electrode be positioned opposite each other in the measuring cell.

In the case of measuring cells which are furnished with more than one electrode system, which systems are placed one behind the other in the flow direction of the sample, it is of advantage to provide each electrode system with a separate device for measuring impedance or conductance, in order to be able to separately monitor positioning and bubble occurrence for each electrode system.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The embodiments of the present invention will now be explained in detail with reference to the attached drawings, in which.

DETAILED DESCRIPTION OF THE INVENTION

Figure 1:
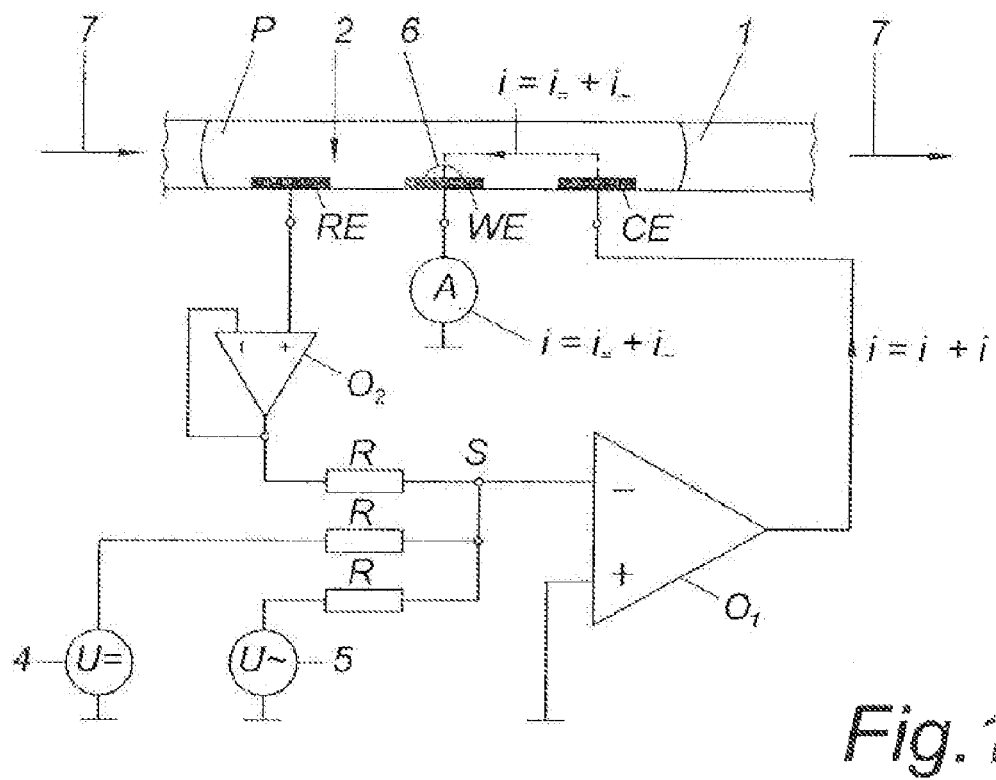
FIG. 1 schematically presents a first variant of a device according to the present invention for the monitoring of the positioning and the absence of bubbles in a medical microsample in a flow cell of an analyzer.

FIG. 1 presents the first variant of a device for the monitoring of position and bubble formation in a medical microsample P in a flow cell or measurement capillary 1 of an analyzer not shown here in detail, where the counter-electrode CE and the working electrode WE of an amperometric electrode system 2 are used as contact points between which the impedance or conductance of the microsample is measured, for instance for the measurement of glucose concentration in a blood sample. Further electrode systems may be placed behind electrode system 2 but are not shown in the drawing.

The circuit realizes a potentiostatic design based on the addition principle. By using an adder the target value of the voltage at the reference electrode RE may be built up by superposition of a number of different input voltages. The operational amplifier $O_1$ varies its output voltage (corresponding to the voltage at the counter-electrode CE) until the sum of the currents at the summation point S(=inverting terminal of the operational amplifier $O_1$) equals zero.

The operational amplifier $O_2$ is configured as a voltage follower (impedance transformer) and is used for high-resistance measurement of the voltage at the reference electrode RE which should not be subjected to current flow. At the output terminal of $O_2$ the reference electrode voltage from a low-resistance voltage source is present and via the resistor R is coupled to the summation point S preceding the operational amplifier $O_1$.

In the present example the reference electrode voltage is built up by superposing a DC component $U_=$ (e.g., 350 mV) and an AC component $U_~$ (e.g., a sinusoidal alternating voltage of 1 kHz with an amplitude of 9 mV r.m.s) indicated in the drawing by a DC voltage source 4 and an AC voltage source 5. Both sources are connected to the summation point S via resistors R. For bubble detection and position-monitoring the optimal choice for the frequency of the AC component lies in the range from 1 kHz to 5 kHz.

At the summation point the following equations hold:

$i_1+i_2+i_3=0$ $i_3=U_~/R$ $i_2=U_=/R$ $i_1=-(i_2+i_3)=-(U_=+U_~)/R$ $U_{RE}=i_{1i}*R=-(U_=+U_~)$ and thus, $U_{RE}=-(U_=+U_~)$ The reference electrode voltage is the sum of the voltages of the voltage sources 4 and 5. Due to the use of the impedance transformer $O_2$ the reference electrode is practically current-free.

The sensor current flows from the output terminal of $O_1$ via the counter-electrode CE, the working electrode WE and the ampere-meter A to ground.

For the evaluation process the DC component (containing the information pertaining to analyte concentration, e.g., glucose concentration) and the AC component (containing the impedance information) are separated by known filter circuits not shown in FIG. 1 (e.g., a band-pass for the AC component and a low-pass for the DC component).

With the device described above the microsample P may be exactly positioned in the area of the electrode system 2 of the measuring cell 1 (correct positioning is indicated by the measured conductance attaining a previously known value). A deviation from the previously known value, caused for instance by an air bubble in the area of the working electrode WE, indicates a disturbance in the system and the necessity of a repetition of the measurement of the relevant substance in the sample.

The direction of sample flow in the measuring cell 1 is indicated by arrows 7. The counter-electrodes are typically placed last in flow direction whilst the sequential placement of the reference electrode and the working electrode may vary with the given application. For single measurements it is typical if the reference electrode RE of each electrode system is wetted first by the microsample. In systems for continuous measurement, where short down-times are desirable, it is typical if the working electrode WE is placed first.

Figure 2:
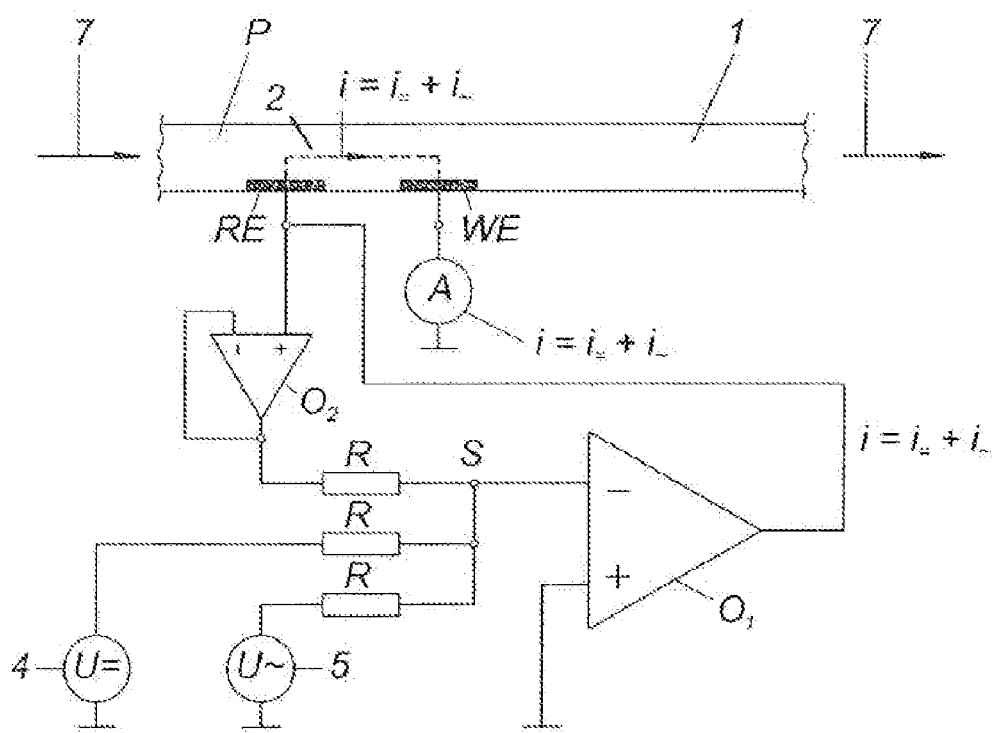
FIG. 2 shows a second variant of a device according to the invention.

In the variant shown in FIG. 2 the measuring cell 1 is provided with an amperometric electrode system 2 consisting of a working electrode WE and a pseudo-reference electrode RE. The potentiostatic three-electrode system of FIG. 1 may be changed into a two-electrode system if the sensor currents arising during analyte determination are very small (order of magnitude of a few nano-amperes).

Regarding the electronic circuit this change is effected by connecting the output terminal of the operational amplifier $O_1$ with the non-inverting input terminal of the operational amplifier $O_2$. Since in the two-electrode system a (small) current flows through the reference electrode RE this electrode is no longer called a reference electrode but rather a pseudo-reference electrode.

A voltage drop across the electrolyte resistance or across the electrode interface resistance of the pseudo-RE is not compensated and will show up at larger sensor currents by a degradation of the region of measurement linearity.

The functionality of the circuit is based on the fact that all control activity is eliminated and that the sum of the voltages from the DC-source 4 and the AC-source 5 is applied to the terminal of the pseudo-RE, such that the sensor current flows from the reference electrode RE via the working electrode WE and the amperemeter A to ground. As regard to the separation of the DC and AC component the description of FIG. 1 applies.

Figure 3:
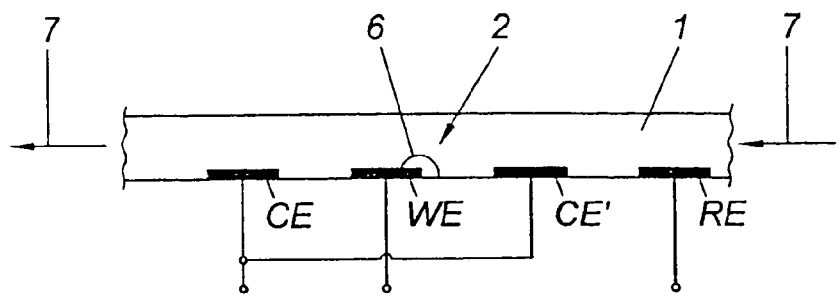
FIGS. 3 and 4 show different electrode systems of a device according to an embodiment of the present invention.

If an air bubble 6 adheres to the edge of the working electrode WE next to the reference electrode RE, it is typical—as shown in FIG. 3—to place yet another counter-electrode CE' between working electrode WE and reference electrode RE and to short-circuit the counter-electrodes CE and CE' electrically, which leads to better detectability of air bubbles in the area.

Figure 4:
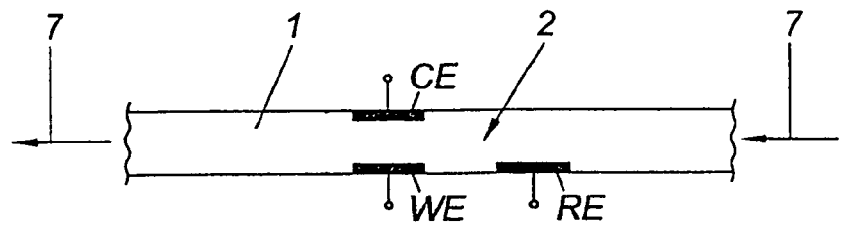

Further advantages will result from positioning the single electrodes as shown in FIG. 4, where working electrode WE and counter-electrode CE are placed opposite each other in the measuring cell or measurement capillary 1. The reference electrode RE may be placed on the side of the working electrode WE (as shown) or it may also be placed on the side of the counter-electrode CE.

Figure 5:
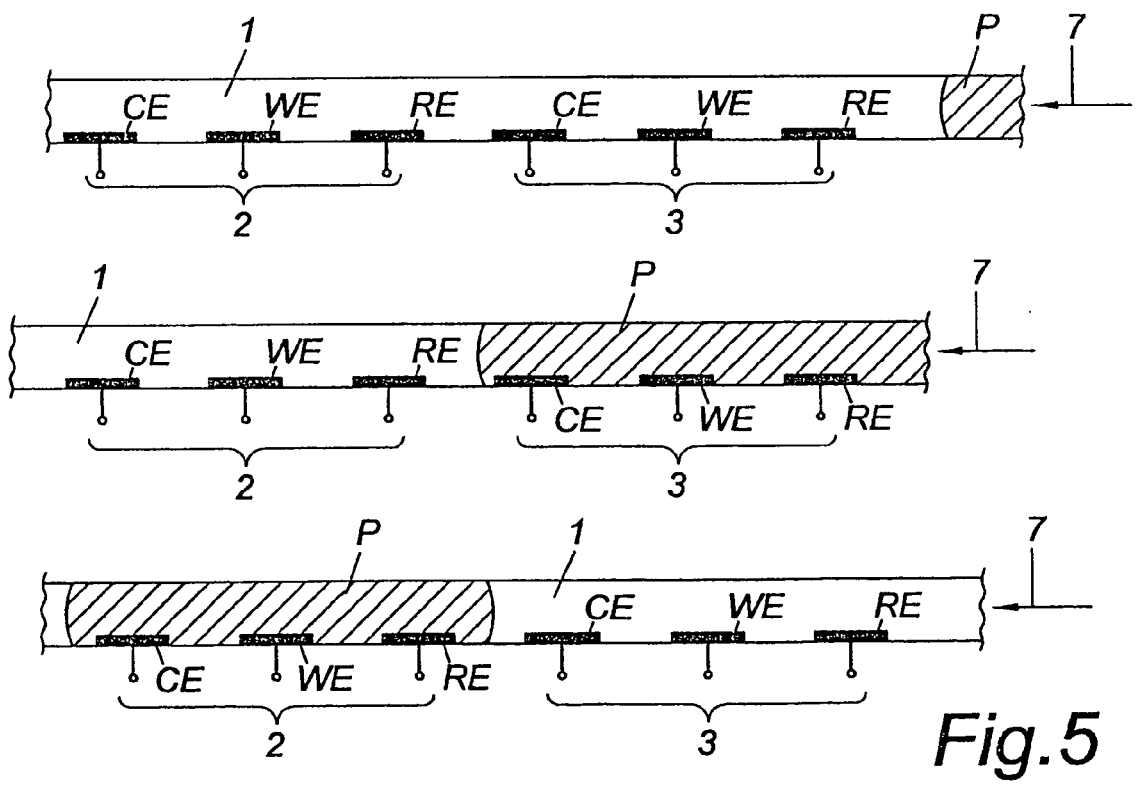
FIG. 5 shows three successive stages of a measurement process with a device according to an embodiment of the present invention.

In FIG. 5 the exact positioning of a microsample P in the measuring cell 1 is shown in various stages, the measuring cell being provided with an electrode system 2, for instance for measuring glucose, and with an electrode system 3, for instance for measuring lactate. As can be seen from this example exact positioning of the microsample in the area of each electrode system 2 or 3 is possible, without the necessity of completely filling the measuring cell with sample fluid. Thus the volume of sample sucked into the measuring cell need only be large enough to ensure wetting of the three-electrode system.

Figure 6:
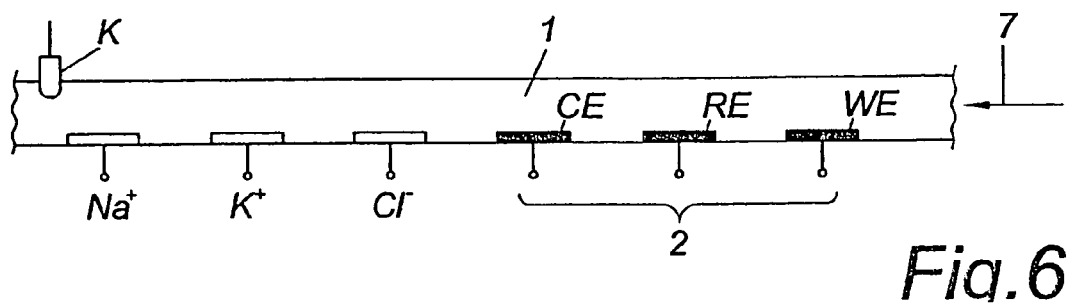
FIGS. 6 and 7 show further electrode systems for a device according to an embodiment of the present invention.

In principle the method of sample positioning and bubble detection described may also be applied with potentiometric electrode systems. As shown in FIG. 6 one and the same measuring cell 1 may be provided with potentiometric electrodes for the measurement of e.g., $Na^+$, $D^+$ and $Cl^-$, in addition to amperometric electrode systems 2 and 3.

The reference electrode RE in the electrode system 2 is placed downstream of the working electrode WE.

Figure 7:
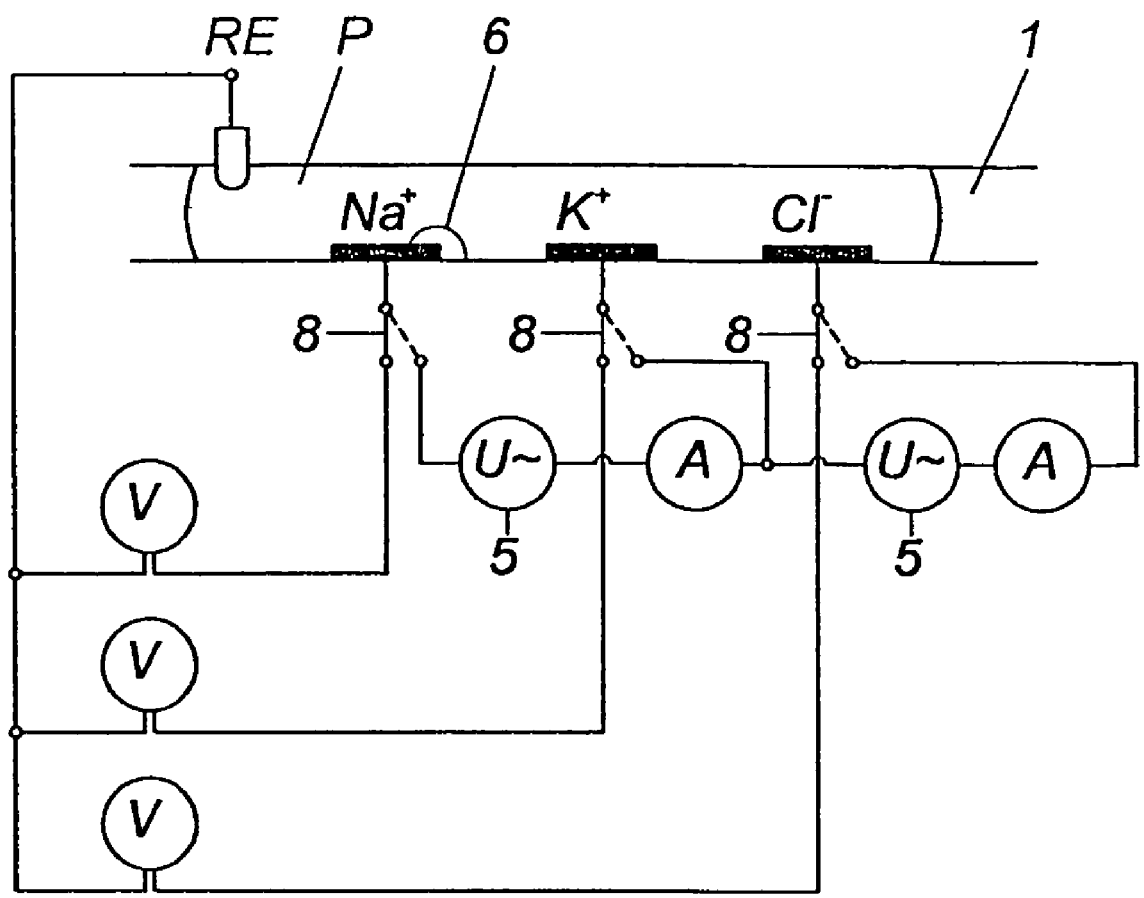

FIG. 7 shows an example of a circuit design in which one may change between analyte measurement and bubble-detection/sample-positioning by means of a switch 8. According to the position of the switch either impedance measurement or analyte determination is performed. Since potentiometric electrodes are characterized by very high resistance and since the Nernst equation describes the electrode potentials for current-free electrodes, any current flow would lead to appreciable deviations from potential equilibrium and thus to disturbances during analyte measurement. For this reason it is of advantage to switch between measurements. The switch might also be realized by fast electronic switches.

The device according to an embodiment of the invention can also be used to measure the impedance of a carrier fluid (perfusion fluid) introduced into the tissue of a patient, after equilibration with the tissue fluid, the impedance value being used to assess the degree of mixing or enrichment.

A change of the substances carried by the carrier fluid may be determined by measuring the impedance or conductance. Such μ-perfusion systems are described in U.S. Pat. No. 5,097,834. The μ-perfusion method uses a thin, biluminal catheter whose exterior wall is perforated. An ion-free perfusion solution is pumped through the interior lumen to the catheter tip, where it is reversed and sucked off via the exterior lumen. The perforations of the exterior wall give rise to an exchange of fluids (diffusion, convection); tissue fluids or interstitial fluids and their substances enter the perfusion flow, which is directed to the catheter outlet and subsequently to the sensor. The degree of enrichment or mixing with ions from the interstitium can be determined by a conductance measurement, since the conductivity of the ion-free fluid and the conductivity of the interstitial fluid are known. This will permit computation of the recovery rate.

Finally, the device may also be used for the measurement of the impedance of the dialysate after dialysis and the measured impedance may be used to compute the recovery rate.

The μ-dialysis method is very similar to the μ-perfusion method described above, apart from the fact that instead of a perforated catheter a catheter is used whose exterior wall is a dialysis membrane. Such membranes have a MW-cutoff of approx. 20,000 Dalton, i.e., they are permeable for low-molecular substances, such as glucose and electrolytes, and the carrier flow in the catheter is enriched with these low-molecular substances by diffusion. A conductance measurement in a sensor downstream of the catheter permits the determination and checking of the recovery rate in analogy to the example given above.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A device for monitoring a microsample in a flow measuring cell of an analyzer comprising:
   at least one electrode system comprising at least two single electrodes positioned within said flow measuring cell, wherein
      said electrode system is configured for measurement of at least one substance contained in the microsample by application of a measurement voltage which is essentially a DC voltage, and detection of absence of bubbles and/or positioning of said microsample by application of an alternating voltage to said flow measuring cell,
      both the alternating voltage and the measurement voltage are simultaneously and directly applied to the single electrodes of the respective electrode system, and
      the measured AC component or the measured impedance provides a measure for the position of the microsample and/or the absence of bubbles; and
   a circuit for producing the voltages to be applied to the single electrodes, which circuit has a summation point at which the alternating voltage for the purpose of monitoring the microsample with regard to position and/or absence of bubbles is superposed on the DC voltage serving as measurement voltage.

2. A device according to claim 1, wherein an electrode system includes a working electrode and a reference electrode, both electrodes serving as electrical contacts for measuring the impedance between working electrode and reference electrode.

3. A device according to claim 1, wherein an electrode system includes a working electrode, a counter-electrode and a reference electrode, the working electrode and the counter-electrode serving as electrical contacts for measuring the impedance between working electrode and counter-electrode.

4. A device according to claim 3, wherein the working electrode is positioned in front of the reference electrode, and the counter-electrode is positioned behind the reference electrode in flow direction of the microsample.

5. A device according to claim 3, wherein counter-electrodes are placed both in front of and behind the working electrode in flow direction of the microsample, both counter-electrodes being electrically short-circuited.

6. A device according to claim 3, wherein the counter-electrode and the working electrode are positioned opposite each other in the measuring cell.

7. A device according to claim 1, wherein the summation point is connected with the inverting input terminal of an operational amplifier.

8. A device according to claim 1, wherein each electrode system is provided with a device for measuring impedance, which is configured as a circuit for superposing an alternating voltage on a DC voltage.

9. A method for monitoring a microsample in a flow measuring cell of an analyzer comprising:
   providing an analyzer including a flow measuring cell and a device comprising at least one electrode system, each said system comprising at least two single electrodes;
   introducing a microsample into said flow measuring cell, said microsample passing said electrode system;
   measuring at least one substance contained in the microsample by applying a measurement voltage to said flow measuring cell, which said measurement voltage is essentially a DC voltage; and
   detecting the absence of bubbles and/or position of said microsample in an area of said at least one electrode system by applying an alternating voltage to said flow measuring cell simultaneous with said measurement voltage via two single electrodes of said at least one electrode system, and detecting the AC component or impedance.

10. A method according to claim 9, wherein the microsample in the flow measuring cell is moved along until a predetermined value for impedance or conductance is obtained, which indicates that the microsample is positioned precisely in the area of the respective electrode system.

11. A method according to claim 9, wherein the sample position and/or absence of bubbles of the microsample are determined in the area of each electrode system.

* * * * *